United States Patent
Thompson et al.

(10) Patent No.: US 7,469,866 B2
(45) Date of Patent: Dec. 30, 2008

(54) APPLIANCE FOR THE HANDICAPPED

(76) Inventors: Tyler M. Thompson, 21498 Elk Lake Rd., Elk River, MN (US) 55330; Joseph R. Jacobs, 411 Washington Ave., Big Lake, MN (US) 55309

( * ) Notice: Subject to any disclaimer, the term of this patent is extended or adjusted under 35 U.S.C. 154(b) by 64 days.

(21) Appl. No.: 11/297,886

(22) Filed: Dec. 9, 2005

(65) Prior Publication Data

US 2006/0186280 A1     Aug. 24, 2006

Related U.S. Application Data

(60) Provisional application No. 60/634,573, filed on Dec. 9, 2004.

(51) Int. Cl.
*B68G 5/00*     (2006.01)
(52) U.S. Cl. .................. 248/118; 248/118.1; 128/877
(58) Field of Classification Search .............. 248/118, 248/118.1, 118.3, 118.5; 128/877, 878, 879; 482/44, 46; 623/57, 61
See application file for complete search history.

(56) References Cited

U.S. PATENT DOCUMENTS

| | | | | |
|---|---|---|---|---|
| 591,800 | A | * | 10/1897 | Finnblade .................. 84/469 |
| 2,884,739 | A | | 5/1959 | Ketcham .................. 46/163 |
| 3,434,163 | A | | 3/1969 | Saverino .................. 3/12.8 |
| 3,942,194 | A | | 3/1976 | Winter .................. 3/1 |
| 4,035,865 | A | | 7/1977 | McRae et al. .............. 16/114 R |
| 4,261,608 | A | | 4/1981 | Bradshaw .................. 294/25 |
| 4,325,187 | A | | 4/1982 | Wasson .................. 30/327 |
| 4,511,272 | A | | 4/1985 | Brown et al. .................. 401/6 |
| 4,602,885 | A | | 7/1986 | Bischoff et al. .................. 401/6 |
| 4,821,417 | A | | 4/1989 | Levine .................. 30/298 |
| 4,911,725 | A | | 3/1990 | Duvieilh .................. 623/65 |
| 4,944,766 | A | | 7/1990 | Williams .................. 623/65 |
| 4,957,442 | A | | 9/1990 | Prater .................. 434/166 |
| 5,163,966 | A | | 11/1992 | Norton et al. .................. 623/65 |
| 5,222,986 | A | | 6/1993 | Wright .................. 623/64 |
| 5,464,444 | A | | 11/1995 | Farquharson et al. ......... 623/65 |
| 5,597,189 | A | | 1/1997 | Barbee, Sr. .................. 294/25 |
| 5,753,840 | A | * | 5/1998 | Saboia De Albuquerque . 84/453 |
| 6,126,696 | A | | 10/2000 | Casto .................. 623/65 |
| 7,156,819 | B2 | * | 1/2007 | Sieller et al. .................. 602/21 |

* cited by examiner

*Primary Examiner*—A. Joseph Wujciak, III
(74) *Attorney, Agent, or Firm*—Nawrocki, Rooney & Sivertson, P.A.

(57)  ABSTRACT

Apparatus to permit handicapped persons with arm and/or hand injury to manipulate a variety of objects. A extension supports a clamp on one end opposite a hand rest on the other. Straps are used to secure the forearm and hand in place on the apparatus. A bar, which extends outwardly from the rest, can have a variety of items attached to permit manipulating them with the apparatus. A supplemental structure can be attached to the apparatus on the side opposite to the clamp and rest with an open channel along the extension to better engage elongated items. Straps can also be used to secure the elongated items within the channel.

8 Claims, 4 Drawing Sheets

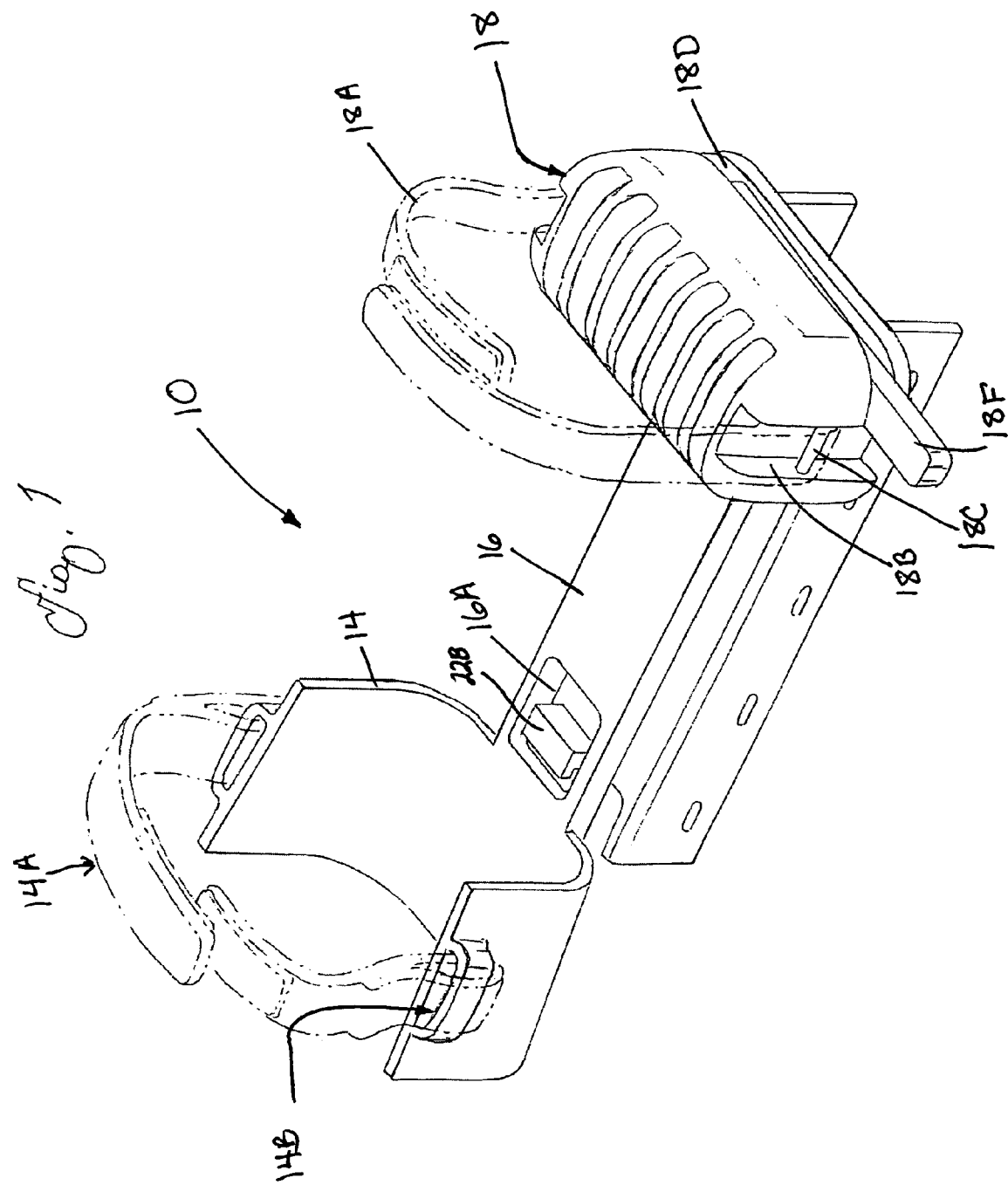

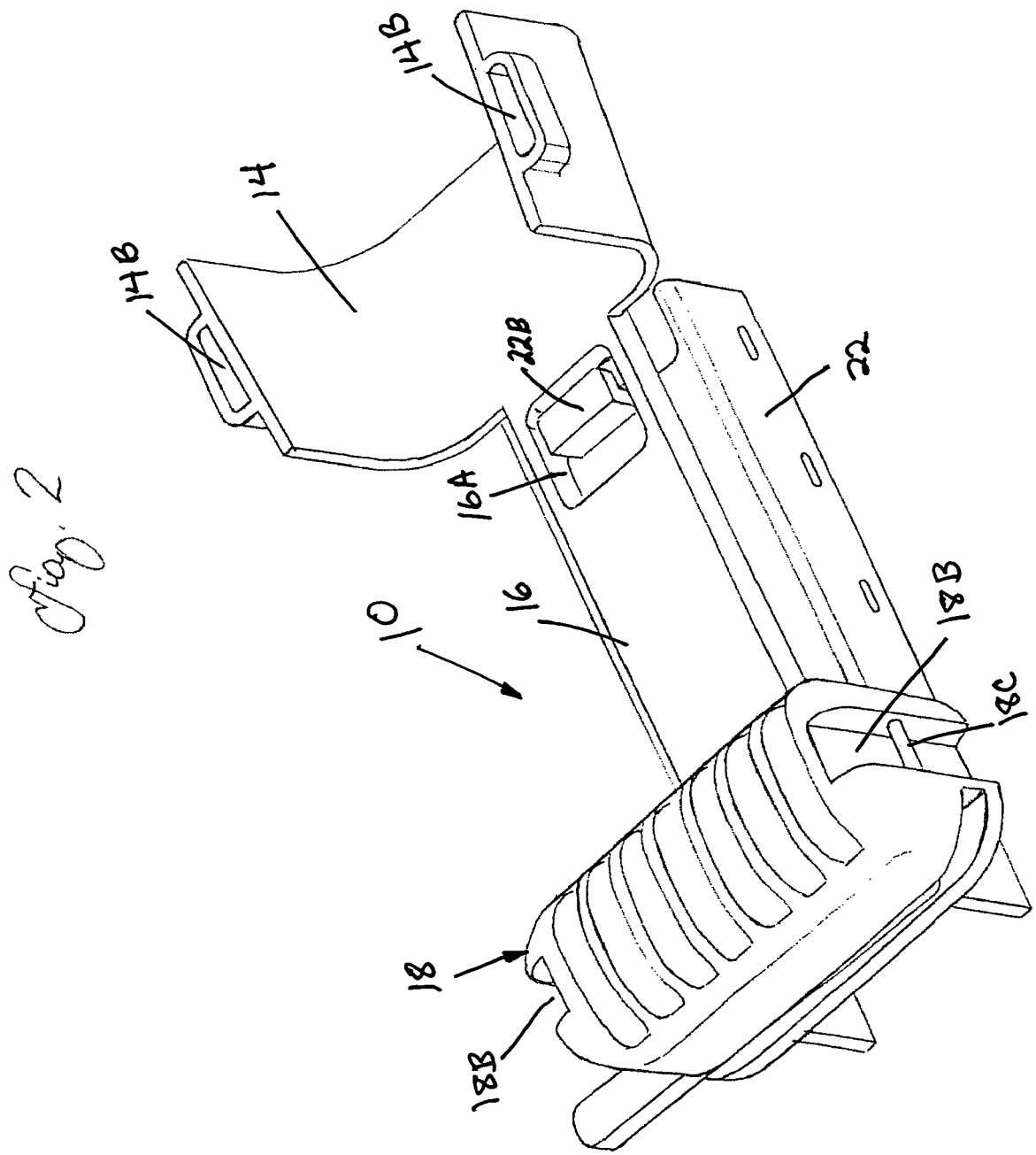

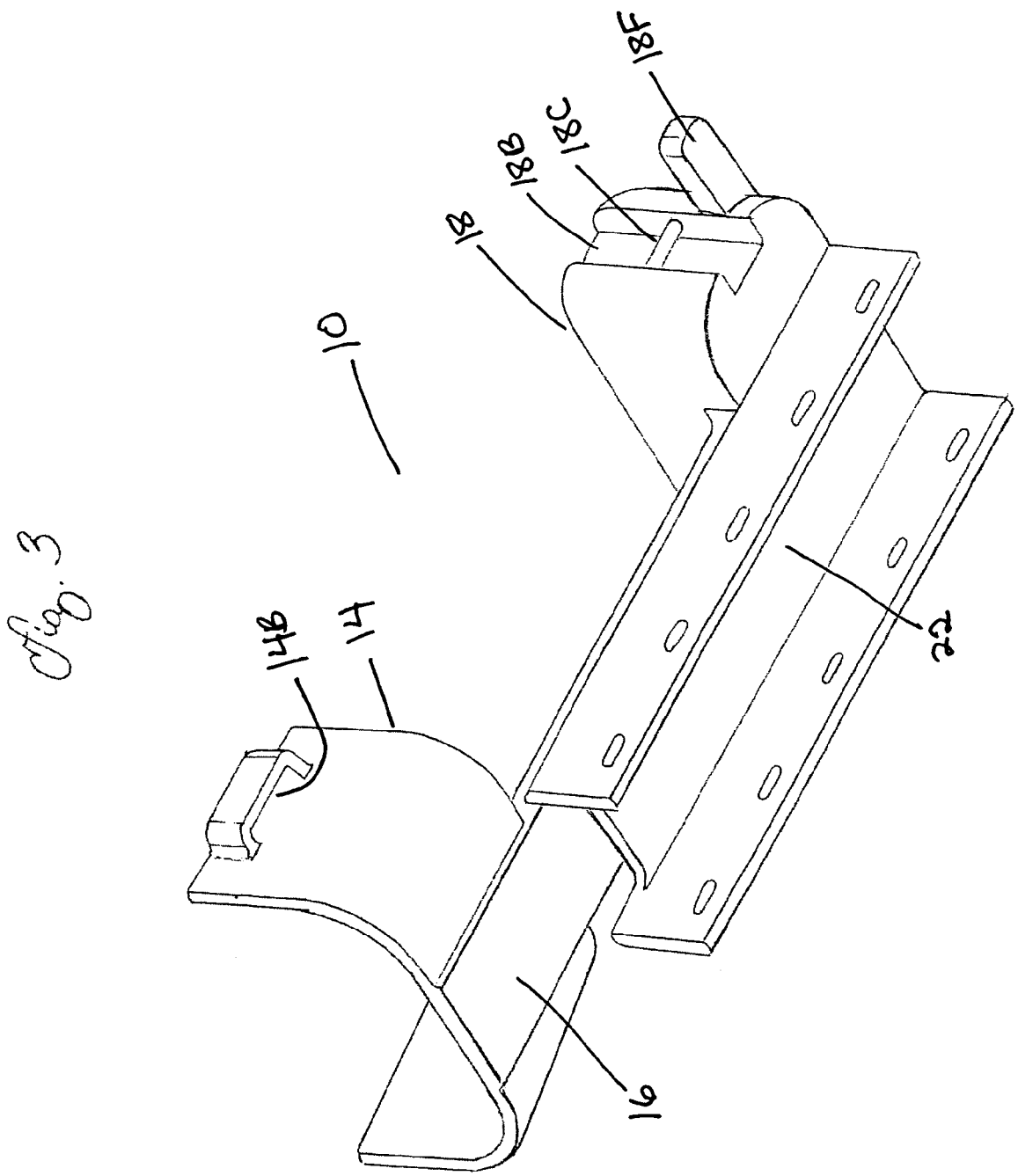

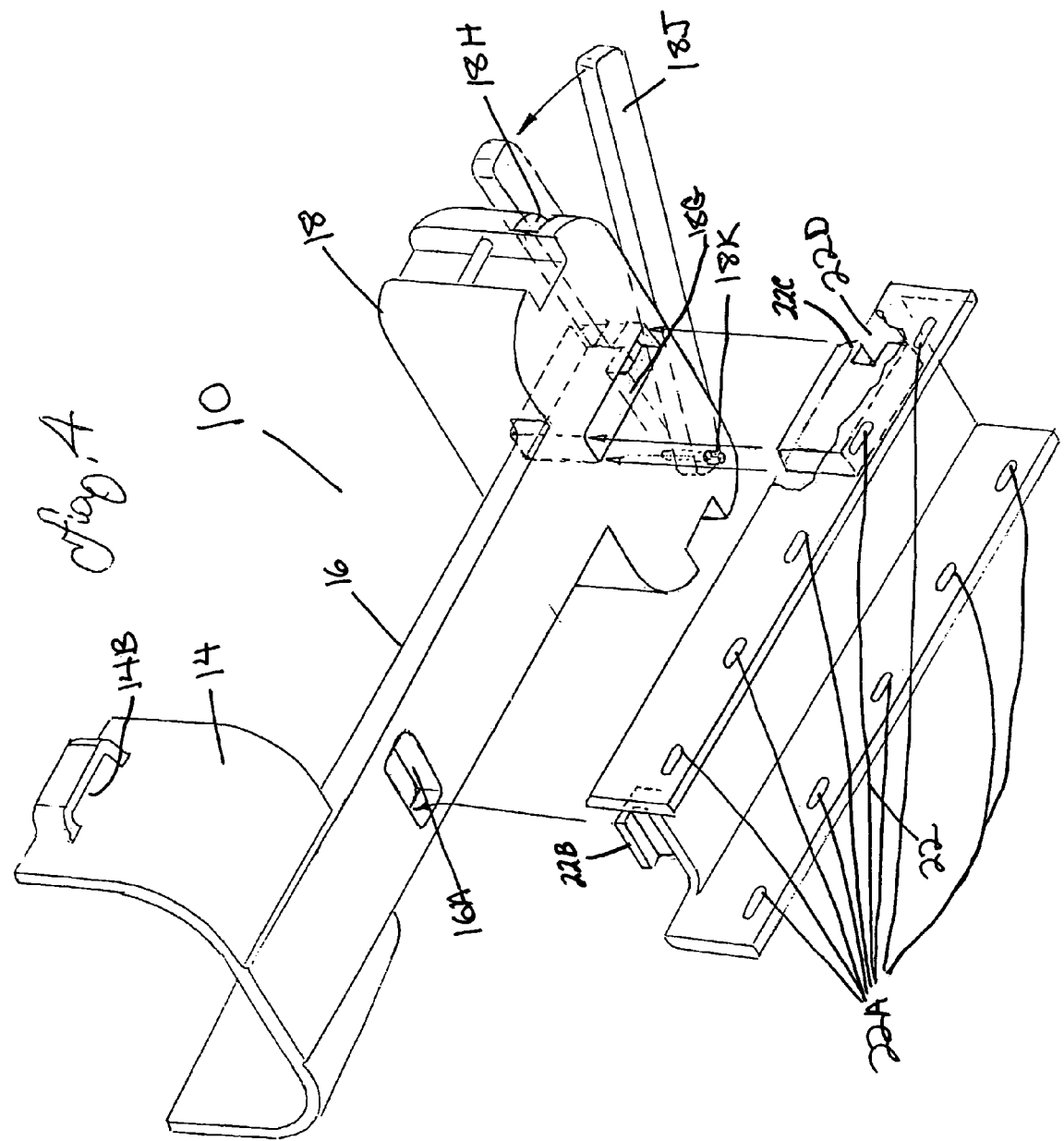

APPLIANCE FOR THE HANDICAPPED

CROSS-REFERENCE TO RELATED APPLICATIONS

This is a regular application filed under 35 U.S.C. § 111(a) claiming priority, under 35 U.S.C. § 119(e) (1), of provisional application Ser. No. 60/634,573, previously filed Dec. 9, 2004 under 35 U.S.C. § 111(b).

BACKGROUND OF THE INVENTION

There are many appliances which are useful for people with a variety of hand injuries or amputations for grasping or manipulating a variety of objects. Typical appliances include ones shown in U.S. Pat. No. 4,821,417 issued Apr. 18, 1989; U.S. Pat. No. 4,957,442 issued Sep. 18, 1990; U.S. Pat. No. 5,163,966 issued Nov. 17, 1992; and U.S. Pat. No. 5,222,986 issued Jun. 29, 1993.

This invention includes an improved prosthetic appliance for people having a limited use of their hands and/or arms in that it provides an essentially ergonomic position of the hand for manipulating a variety of objects in two different ways.

SUMMARY OF THE INVENTION

This invention includes an apparatus arranged to be attached to a forearm to permit utilizing an injured arm or hand. The apparatus consists of a base having a U-shaped clamp on one end sized to provide a receiver to engaging a forearm, and a hand rest on the opposite end sized to provide a rest for the palm of a hand. Straps encircling the clamp and rest hold the respective forearm and palm in place on the base. This arrangement provides a natural ergonomic position of the hand with respect to the arm. An outwardly extending holding bar 18F can be slid into a recess on the rest near the palm of the hand. Bar 18F can be slid to extend outwardly from rest 18 in either direction to depending upon whether the right or the left hand is positioned over the rest. Bar provides a location for a variety of different items to be attached for manipulation of the item by the injured hand of the user in a natural ergonomic arrangement. A supplemental structure, which presents an outwardly open channel, can be attached to the apparatus to hold a variety of elongated items. The channel has a provision for securing these items within the channel. The possibility of two separate locations and arrangements for connecting various items to be manipulated greatly extends the use of this apparatus.

BRIEF DESCRIPTION OF THE DRAWINGS

FIG. 1 is a first top isometric view of the apparatus with the structure attached;

FIG. 2 is a second top isometric view of the apparatus with the structure attached;

FIG. 3 is a bottom isometric view of the apparatus with the structure attached; and FIG. 4 is a bottom isometric view of the apparatus with the structure detached.

DETAILED DESCRIPTION OF THE INVENTION

FIGS. 1, 2, 3 and 4 show apparatus 10 made up of an extension 16 with an essentially U-shaped clamp 14 on one end and a hand rest 18 on the other end opposite each other. Clamp 14 is sized to receive the forearm of a user. Clamp 14 has slot openings 14B on opposite ends sized to receive a first strap 14A. The purpose of first strap 14A is described later. First strap 14A has opposed velcro attachments to secure the ends together over the forearm of a user.

Hand rest 18 is sized to provide a rest for the palm of a user. Recesses 18B on opposite sides of hand rest 18, which are perpendicular to the span of extension 16 between clamp 14 and rest 18, are sized to receive a second strap 18A. Second strap 18A also has opposed velcro attachments to secure the ends together. Strap retainers 18C within recesses 18B secure second strap 18A within recesses 18B. Rest 18 has a groove 18D sized to hold bar 18F securely in place. Bar 18F can be slid along groove 18D to extended from either side of rest 18 for right or left hand use.

When used without removable supplemental structure 22, which is described later, the forearm is place over extension 16 with the palm of the hand on hand rest 18. First strap 14A is then placed around the forearm and secured in place by the velcro connectors on the end. Second strap 18A is placed through recesses 18B and under strap retainers 18C and over the hand and secured in place by velcro connectors on the end. Bar 18F is slid into groove 18D with the appropriate end extending for the right or left hand such that the bar extends in the same direction as the thumb of the hand. The item to be manipulated is attached to the portion of bar 18F which extends outwardly from rest 18. This arrangement permits a user to readily manipulate the item attached to bar 18F using apparatus 10.

The remaining discussion related to a detachable supplemental structure 22 which is useful for manipulating elongated items. Extension 16 has a first rectangular opening 16A. A rectangular second opening 18G extends completely through rest 18. Structure 22 has a first projection 22B extending outwardly from one end and a second projection 22C extending outwardly in the same direction from the opposite end. Projection 22B has an L-shaped cross-section with an outward extension at the end.

Structure 22 can be attached to apparatus 10 by first placing them in the relationship shown in FIG. 4. Structure 22 is then inclined and the end of first projection 22B inserted into opening 16A which is oriented and sized to receive the projection in the relationship shown. Structure 22 is then placed adjacent to apparatus 10 which locates second projection 22C into rectangular opening 18J, which is oriented and sized to receive the projection in the relationship shown.

Rest 18 has a first locking slot 18H across the side opposite clamp 14. First locking slot 18H is sized to accept the cross-section of locking arm 18J, which pivots around pin 18K in or out of the slot in the relationship shown in FIG. 4. Second projection 22C has a rectangular cross section opposite second locking slot 22D on the end opposite first projection 22B which is sized to accept the cross-section of locking arm 18J in the relationship shown in FIG. 4. Before structure 22 is attached to apparatus 10, locking arm 18J is rotated outwardly clear of first locking slot 18H and second locking slot 22D. After structure 22 has been located adjacent to apparatus 10, locking arm 18J is rotated into first locking slot 18H and second locking slot 22D to secure the structure to the apparatus. Structure 22 is removed from apparatus 10 by simply reversing this process.

Structure 22, which has outwardly extending parallel sides in the relationship shown in FIG. 4, has a number of opposed pairs of retaining slots 22A through the sides. Straps or cords can be extended through opposed slots 22A in structure 22 at various locations to secure elongated items extending along the length of the structure. This arrangement permits a user to readily manipulate an elongated item attached to structure 22 using apparatus 10.

This arrangement of the apparatus 10 and the alternate addition of structure 22 provides the user with a ready means to manipulate a large variety of items in an ergonomic manner.

The above is an example of the possible ways of achieving the same results, and which would readily occur to one skilled in the art, therefore it is contemplated that the appended claims will cover any such modifications or embodiments as fall within the true scope of the invention.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. Apparatus for manipulating objects, comprising:
a) an extension having a first dimension between a first and a second end;
b) an essentially U-shaped clamp attached to the first end of said extension with the open end outward, the clamp being sized and attached to receive the forearm portion of an arm extending along the first dimension of the extension from the first end to the second end with the hand opposite the second end, further comprising first securing means for securing the forearm within the clamp;
c) a hand rest located on the second end of the extension on the same side of the extension as the clamp, the hand rest being sized and arranged to provide a rest for the palm of the hand of a forearm extended along the extension, further comprising second securing means for securing the hand to the rest; and
d) a bar and bar attachment means for attaching the bar to the rest, the attachment means being arranged to permit the bar to extend outwardly in either direction from the rest essentially perpendicular to the first dimension of the extension wherein the bar detaches extension from a supplemental structure;
(e) wherein said second securing means comprises a second strap, with said rest having grooves on opposite sides which are perpendicular to the first dimension of the extension, being sized to admit the second strap, with the groves, the rest and the second strap being sized and arranged to permit the strap to encircle the rest and a hand positioned on the rest and secure the hand to the rest with the palm of the hand facing the rest.

2. Apparatus as in claim 1 wherein the first securing means comprises a first strap with the clamp having slot openings on the opposite sides which are perpendicular to the first dimension of the extension, the openings being sized to admit the first strap, the slot openings having retainers arranged to secure a strap within the slot, with the clamp, the slot openings, the slot retainers and the first strap being sized and arranged to permit the first strap to encircle the extension and the forearm and secure the forearm within the clamp.

3. Apparatus as in claim 1 further comprising a supplemental structure, the structure being elongated along a first dimension between a first and second end having essentially the length as the extension, the supplemental structure having an essentially U-shaped cross-section with an essentially planar web connecting two planar sides, the apparatus having structure attaching means for attaching the structure to the extension essentially in alignment therewith, with the structure having item attachment means for attaching items within and between the sides.

4. Apparatus as in claim 3 wherein said structure has a first and a second end and wherein said attachment means comprises the extension having a rectangular opening with the structure having an L-shaped first projection near a first end thereof with the end of the projection facing outwardly, a first orientation of the structure and extension having the opening located such that the ends of the structure and extension will be essentially adjacent to each other when the structure is located with the web adjacent to the extension, the opening being sized to receive the end of the first extension, the rest having a rectangular shaped second opening and the structure having an extension with a rectangular cross-section, the extension and the second opening being sized and located such that, when the structure and extension are in the first orientation, a second projection and the second opening will mate with each other, the rest and the structure having locking slots which are parallel to each other along the sides opposite to the clamp, the rest having a locking arm pivotably mounted about one end therewithin, which engages the locking slot of the structure when the structure and the extension are in the first orientation and the arm is pivoted towards the structure.

5. Apparatus as in claim 3 wherein the item attachment means comprises a plurality of opposed pairs of slots spaced along the sides of the structure.

6. Apparatus for manipulating objects, comprising:
a) an extension having a first dimension between a first and a second end;
b) an essentially U-shaped clamp attached to the first end of said extension with the open end outward, the clamp being sized and attached to receive the forearm portion of an arm extending along the first dimension of the extension from the first end to the second end with the hand opposite the second end, further comprising first securing means for securing the forearm within the clamp;
c) a hand rest located on the second end of the extensin on the same side of the extension as the clamp, the hand rest being sized and arranged to provide a rest for the palm of the hand of a forearm extended along the extension, further comprising second securing means for securing the hand to the rest; and
d) a bar and bar attachment means for attching the bar to the rest, the attachment means being arranged to permit the bar to extend outwardly in either direction from the rest essentially perpendicular to the first demension of the extension wherein the bar detaches extension from a supplemental structure;
e) wherein the rest has a cross-dimension perpendicular to the first dimension of the extension, the rest having a groove extending completely therethrough which is essentially parallel to the cross-dimension of the rest, the groove being sized and arranged to permit attaching the bar securely within the groove, the bar having a length greater than the length of the groove to permit one end of the bar to extend outwardly from the rest arranged to provide an attachment location for external items on either side of the rest.

7. Apparatus as in claim 6 wherein the first securing means comprises a first strap with the clamp having slot openings on the opposite sides which are perpendicular to the first dimension of the extension, the openings being sized to admit the first strap, the slot openings having retainers arranged to secure a strap within the slot, with the clamp, the slot openings, the slot retainers and the first strap being sized and arranged to permit the first strap to encircle the extension and the forearm and secure the forearm within the clamp.

8. Apparatus as in the claim 6 the supplemental structure being elongated along a first dimension between a first and second end having of essentially the length as the extension, the supplemental structure having an essentially U-shaped cross-section with an essentially planar web connecting two planar sides, the apparatus having structure attaching means for attaching the structure to the extension essentially in alignment therewith, with the structure having item attachment means for attaching items within and between the sides.

* * * * *